(12) United States Patent
Brandt et al.

(10) Patent No.: US 8,292,617 B2
(45) Date of Patent: Oct. 23, 2012

(54) DENTAL WIRE ATTACHMENT

(75) Inventors: Douglas Brandt, San Pablo (CR); Rick M. Matty, Scotts Valley, CA (US)

(73) Assignee: Align Technology, Inc., San Jose, CA (US)

( * ) Notice: Subject to any disclaimer, the term of this patent is extended or adjusted under 35 U.S.C. 154(b) by 242 days.

(21) Appl. No.: 12/407,072

(22) Filed: Mar. 19, 2009

(65) Prior Publication Data

US 2010/0239992 A1    Sep. 23, 2010

(51) Int. Cl.
*A61C 7/08* (2006.01)
(52) U.S. Cl. .............................. 433/6; 433/22
(58) Field of Classification Search .............. 433/24, 433/5–6, 8–11, 22
See application file for complete search history.

(56) References Cited

U.S. PATENT DOCUMENTS

| | | | | |
|---|---|---|---|---|
| 6,572,372 B1 * | 6/2003 | Phan et al. | | 433/6 |
| 7,020,963 B2 * | 4/2006 | Cleary et al. | | 29/896.11 |
| 7,121,825 B2 * | 10/2006 | Chishti et al. | | 433/6 |
| 2004/0009449 A1 * | 1/2004 | Mah et al. | | 433/7 |
| 2007/0054237 A1 * | 3/2007 | Neuschafer | | 433/37 |

* cited by examiner

*Primary Examiner* — Cris L Rodriguez
*Assistant Examiner* — Matthew Seward
(74) *Attorney, Agent, or Firm* — Brooks, Cameron & Huebsch, PLLC

(57) ABSTRACT

Methods and devices utilizing a dental appliance for dental retainer wire attachment are disclosed. One such wire attachment appliance includes a shell having one or more cavities formed therein and shaped to receive one or more teeth, at least two wire attachment members provided on the shell, and at least one attachment material reservoir provided on the shell, wherein the attachment material is provided to attach a wire to a tooth adjacent to a particular reservoir of the at least one attachment material reservoir.

26 Claims, 7 Drawing Sheets

DENTAL WIRE ATTACHMENT

BACKGROUND

The present disclosure is related generally to the field of dental treatment. More particularly, the present disclosure is related to attachment of a dental wire within a patient's mouth.

Various dental procedures move or adjust the position of teeth within a patient's mouth. When teeth have been moved, for example, to correct a dental malocclusion, once the movement and/or positioning of the one or more teeth is finished, if preventive measures are not taken, the teeth can also move to reproduce the original condition, to some intermediate position between the initial position and the final position attained after the procedures, or to a position that is not part of the treatment.

In such instances, a retainer can be used to prevent the adverse movement of the one or more teeth. The goal of the retainer is to stabilize the new configuration of the teeth so that the teeth do not move to one of the above incorrect positions.

Retention is useful because the bone around the teeth have to rebuild around the new position of the teeth in order to stabilize the teeth. Retention can be accomplished by use of a retainer that holds the teeth in position for a duration of time to allow for the periodontal ligaments and bone to reform around the new positions of the teeth.

In some instances, the periodontal ligaments and bone can, for example, need a number of years for stabilization. In order to provide such long term retention, a fixed retainer is often utilized where two ends of a metallic wire are attached between two teeth and the wire acts to keep the two teeth positioned with respect to each other. Additionally, the wire also can keep teeth in position that are positioned between two teeth at which the two ends of the wire are attached.

The attachment is often accomplished through the mounting of a band around each tooth and the ends of a wire attached to the bands or through the bonding of the ends of the wire to the teeth. These types of attachment methods are performed by the treatment professional and the retainers are shaped by the treatment professional just prior to attachment to the patient's teeth.

Accordingly, in some instances this can lead to imprecise positioning, poor adjustment prior to attachment, and other such problems. These processes can be difficult to perform and can also require special knowledge by the treatment professional to perform and/or specialized materials to implement.

DETAILED DESCRIPTION

Methods and devices for attachment of a wire for a dental retainer are disclosed. For example, one such embodiment of a wire attachment appliance includes a shell having one or more cavities formed therein and shaped to receive one or more teeth.

The embodiment also includes at least two wire attachment members provided on the shell, and at least one attachment material reservoir provided on the shell. In such embodiments, the attachment material is provided to attach a wire to a tooth adjacent to a particular reservoir of the at least one attachment material reservoirs.

In some instances, it may be beneficial to utilize information about the patient's teeth before creating the wire attachment appliance. For example, data about the patient's teeth can be utilized to create a virtual model of some of all of the teeth of the patient.

The virtual model can be created on a computing device through use of a processor, memory, and a number of executable instructions utilized to create the virtual model and display the model on a display device. In such embodiments, this virtual model can be used, for example, to understand how the wire attachment appliance is going to work, how it is going to fit, where it is going to be positioned, and/or other beneficial functions.

Figure 1:
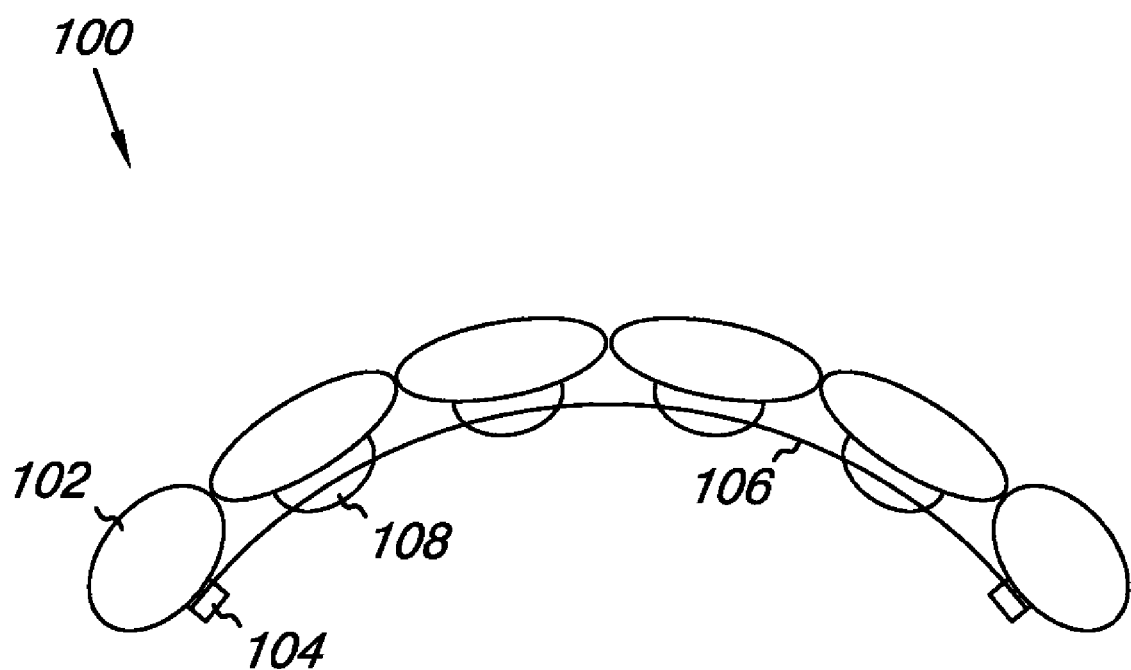
FIG. 1 illustrates a virtual model of attachment of a wire according to an embodiment of the present disclosure.

FIG. 1 illustrates a virtual model of an attachment for a wire according to an embodiment of the present disclosure. In the embodiment illustrated in FIG. 1, a virtual model 100 displays a patient's mouth that is modeled illustrating a number of teeth 102 therein and their orientation with respect to each other.

Such a virtual model can be used to establish the position of the wire on the teeth and can be used to design the attachment components in order to attach the wire to the teeth that are to be retained. For example, in the embodiment illustrated in FIG. 1, a wire 106 is provided in the virtual model 100.

The wire 106 is attached to the teeth by a wire attachment member 104 positioned on each end. It should be noted that more or less attachment members can be utilized and that the attachment members may be positioned on teeth other than those illustrated. Further, any suitable type of wire can be utilized, such as metallic, composite, or polymer wires (e.g., single or multiple strands).

Also illustrated in the embodiment shown in FIG. 1 are a number of attachment members 108 for attachment of the wire 106 to the teeth. The formation of the attachment members is discussed in more detail below.

Figure 2A:
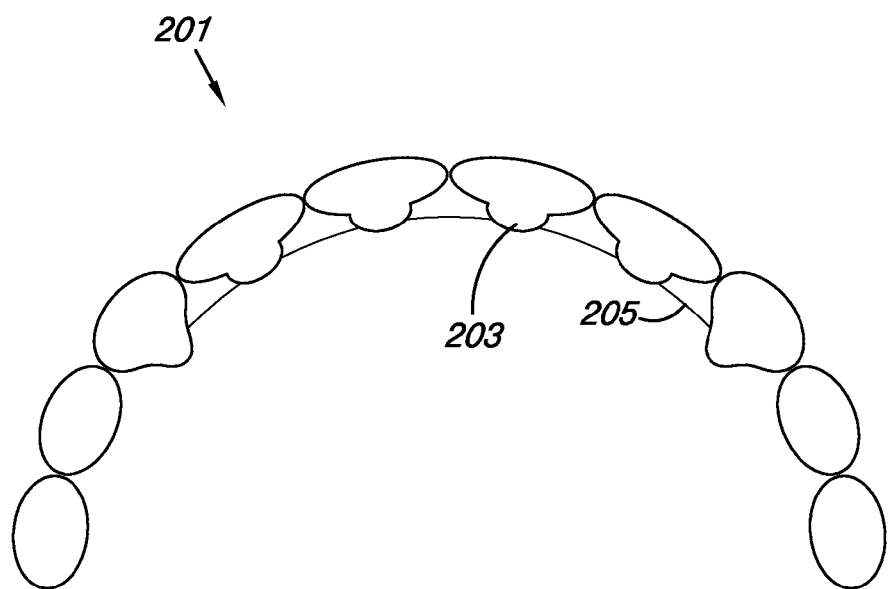
FIG. 2A illustrates a top view of a physical model utilized to form the appliance according to an embodiment of the present disclosure.

FIG. 2A illustrates a physical model with having a number of shapes used to form a number of reservoirs to form the attachment members therein. In some embodiments, the physical model can also include a wire or a shape that is designed to fit over the wire or portions thereof. In addition to aiding in the formation of the appliance, a physical model can be beneficial, for example, to understand how the wire attachment appliance is going to work, how it is going to fit, where it is going to be positioned, and/or other beneficial functions.

As discussed above, the physical model can be used in the fabrication of the wire attachment appliance. In some such embodiments, the wire attachment members are attached to the teeth of the physical model before removal and placement in the patient's mouth. In embodiments, such as that shown in FIGS. 2A and 2B, the physical model 201 includes physical model portions 203 that provide a number of shapes used to form a number of reservoirs to form the attachment members therein and shapes 205 used to form a shape that is designed to fit over the wire or portions thereof.

The physical model can be made from any suitable material. For example, a suitable material can be a material used to form the model through a rapid prototyping technique (e.g., additive manufacturing process), such as by a stereo lithography process, photo lithography process, fused deposition modeling, selective laser sintering, or other such process, among other suitable materials.

Further, the attachment of the wire attachment members can be accomplished in any suitable manner. For example, adhesives, resins, and other suitable materials can be used. In some embodiments, the wire attachment members can be releasably attached (e.g., through use of a releasable adhesive or resin) and, therefore, can be removed for placement in the patient.

In some embodiments, it may be possible to separate the attachment members in another manner and, therefore, a non-releasable attachment type can be formed. For instance, the bond of the adhesive or resin can be broken to remove the attachment members, in some embodiments.

Figure 2B:
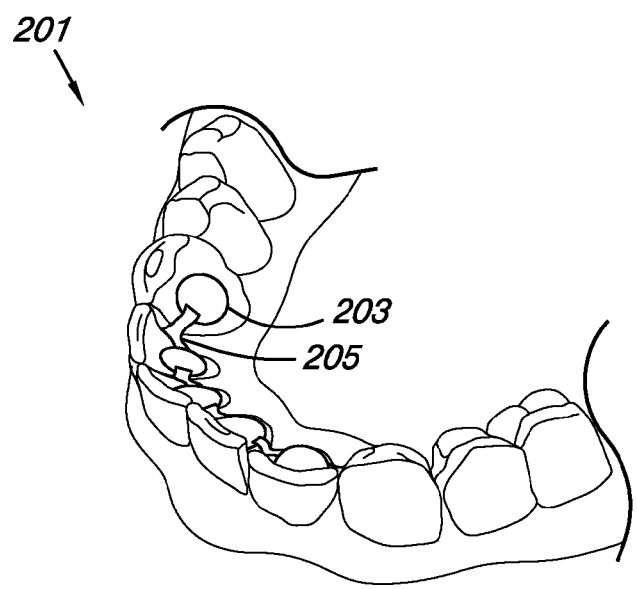
FIG. 2B illustrates an angled side perspective view of a physical model utilized to form the appliance according to an embodiment of the present disclosure.

In the embodiment of FIGS. 2A and 2B, the physical model does not include the actual attachment members, but rather includes portions of the physical model used to form the spaces that will be used to position the actual attachment members. In such embodiments, once the appliance is formed and removed from the physical model, the attachment members can be positioned therein.

Figure 3A:
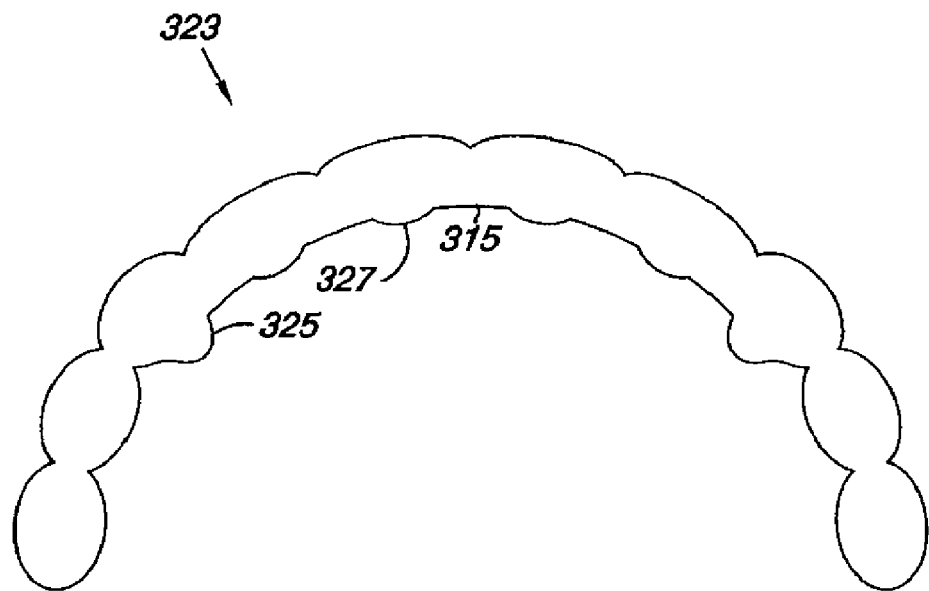
FIG. 3A illustrates a top view of an appliance according to an embodiment of the present disclosure.

FIG. 3A illustrates a top view of an appliance according to an embodiment of the present disclosure. As illustrated in FIGS. 2A and 2B, the appliance 323 can be formed over the physical model of the patient's teeth (e.g., model 201 of FIGS. 2A and 2B).

This can be accomplished, for example, after the wire attachment members and/or the wire have been affixed to the physical model or the physical model is formed having the above discussed reservoir and wire shapes. In such embodiments, for example, a polymeric sheet could be placed over the physical model and then cured to create the appliance 323 having portions forming the reservoirs 325 and 327 and wire accommodating structures 315.

Providing such an appliance could also be accomplished in other manners, such as during a rapid prototyping process. In various embodiments, the appliance can be formed from a rapid prototyping material as discussed above or other suitable manufacturing material, such as polymers, composites, metallic materials, and the like.

As illustrated in FIG. 3A, once formed, the wire can be attached to the wire attachment members after the appliance is formed. For instance, this could be the case when rapid prototyping is used to form the appliance or when a physical model is used that does not utilize the actual attachment members and/or wire.

This attachment can be accomplished during fabrication or by a treatment professional before installation into the patient's mouth, in some embodiments. In various embodiments, the attachment blocks may also be positioned in the appliance by a treatment professional.

In some embodiments, the appliance can be formed independently from the physical model, for example, through some types of rapid prototyping. In some such embodiments the wire attachment members can be attached to the appliance without use of a physical model.

When a physical model is utilized, the wire attachment members can be affixed to the appliance during the formation of the appliance. This can be, for example, via a physical or chemical affixation mechanism and can be releasable, such as by photo resist or chemical resist, in some embodiments, as discussed above. This can be beneficial in some instances, for example, to aid in checking the positioning of the actual wire and attachment members on the physical model. However, in some instances, the virtual modeling can provide such functionality before the physical model is formed.

Figure 3B:
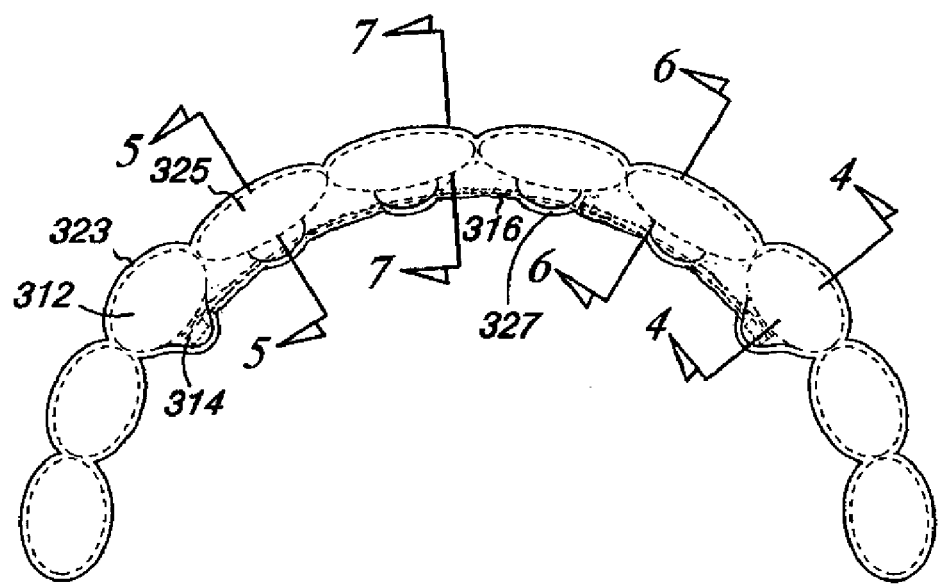
FIG. 3B is a top view illustrating the appliance cavities of an appliance positioned over a patient's teeth according to an embodiment of the present disclosure.

FIG. 3B is a top view illustrating the appliance cavities of an appliance positioned over a patient's teeth according to an embodiment of the present disclosure. The appliance 323, of FIG. 3B, is positioned over a number of teeth (e.g., teeth 312 and 325) and contains a number of spaces for the placement of wire attachment members 314 therein. These wire attachment members are used to position the wire 316 with respect to the patient's teeth in preparation for further securement to the patient's teeth with attachment members formed by the insertion of attachment material in the number of reservoirs 327. As will be described below, the attachment material can be provided to further secure the wire to the teeth of the patient (e.g., the teeth of the patient in which the physical model teeth 312 and 325 were modeled after).

Figure 4:
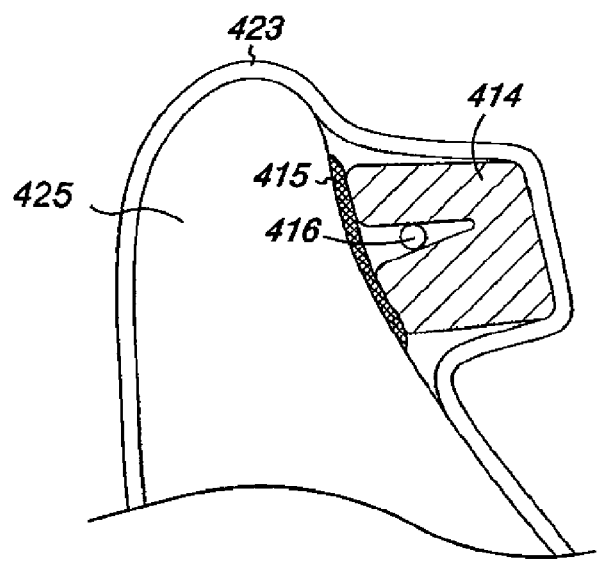
FIG. 4 illustrates a side cut away view taken along line 4-4 of the appliance of FIG. 3B.

FIG. 4 illustrates a side cut away view taken along line 4-4 of the appliance of FIG. 3B. In the embodiment illustrated in FIG. 4, a wire attachment member 414 (e.g., 314 from FIG. 3) is attached to the tooth 425 via an attachment agent 415 (e.g., adhesive, resin, etc.).

In some such embodiments, the attachment member 414 can also be attached to the appliance 423. The appliance may also be formed such that the attachment member is held in place by the appliance material that is formed around the attachment member.

As illustrated in the embodiment of FIG. 4, a portion of the wire 416 can be provided within the wire attachment member 414 provided in the shell of the appliance 423, such that the wire attachment member 414 can be used to hold the wire 416 in position with respect to the teeth of the patient (e.g., the teeth of the patient in which the physical model teeth 425 were modeled after). The positioning of the wire can be accomplished during or after the fabrication on the shell, as will be discussed below.

As discussed above, in some embodiments, the wire attachment members 414 can be affixed to the teeth 425 in various manners. In the embodiment of FIG. 4, a releasable adhesive 415 is used. In such embodiments, once the adhesive is released or is broken, the appliance 423 with wire attachment members 414 and, in some cases, wire 416, can be removed from the mouth of the patient.

Figure 5:
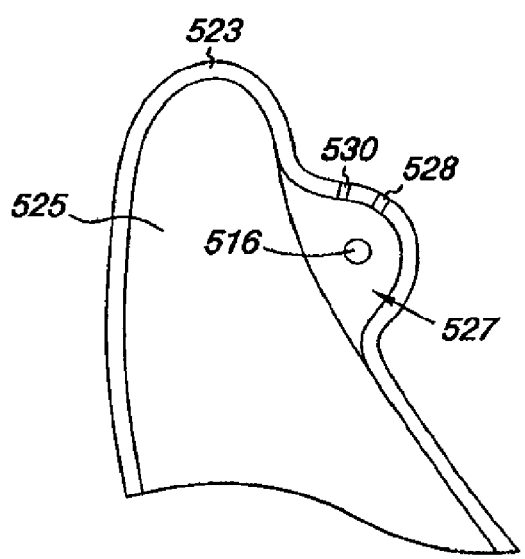
FIG. 5 illustrates a side cut away view taken along line 5-5 of the appliance of FIG. 3B.

FIG. 5 illustrates a side cut away view taken along line 5-5 of the appliance of FIG. 3B. In the embodiment of FIG. 5, the appliance 523 includes an attachment material reservoir 527. In some such embodiments as is illustrated in FIG. 5, the attachment reservoir 527 allows for a portion of the wire 516 to be positioned through the attachment reservoir 527.

This can be accomplished, for example, by placing a slit in the each side of the reservoirs that is sized to allow the wire to be slid through the slit. Accordingly, in some embodiments, the wire 516 may be positioned in the appliance 523 after the appliance is formed. One such example slit configuration is discussed with respect to FIG. 6.

In the embodiment of FIG. 5, the reservoir 527 also includes one or more apertures (e.g., 528 and/or 530) formed therein. These apertures can be used, for example, for the placement of a needle tip or other applicator therein for the purpose of providing the attachment material to the reservoir 527.

In some embodiments, one or more apertures can also be used as vents to allow air to exit the appliance as the attachment material is introduced into the reservoir 527. In some embodiments, these apertures can be formed by the treatment profession, for example, by a needle tip or other applicator or cutting device.

Figure 6:
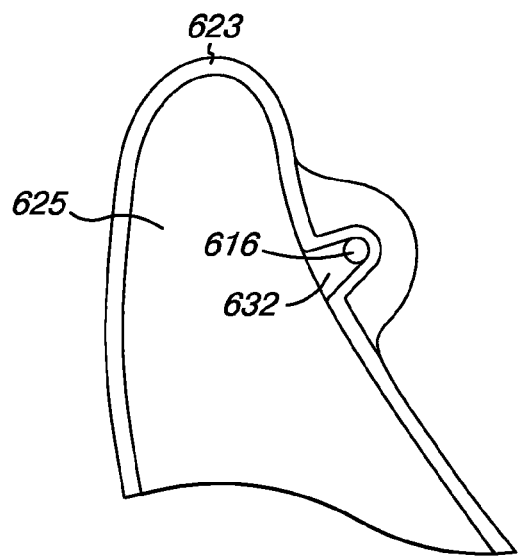
FIG. 6 illustrates a side cut away view taken along line 6-6 of the appliance of FIG. 3B.

FIG. 6 illustrates a side cut away view taken along line 6-6 of the appliance of FIG. 3B. In FIG. 6, the reservoir (e.g., reservoir 527 of FIG. 5) includes a slit 632 in each side of the reservoir, as described above, to allow appliance 623 to be lifted over the wire 616 once the attachment material has been positioned within the reservoir and is solid enough to maintain its shape and adhere to the tooth 625 without the shell of the reservoir positioned to contain the attachment material.

Figure 7:
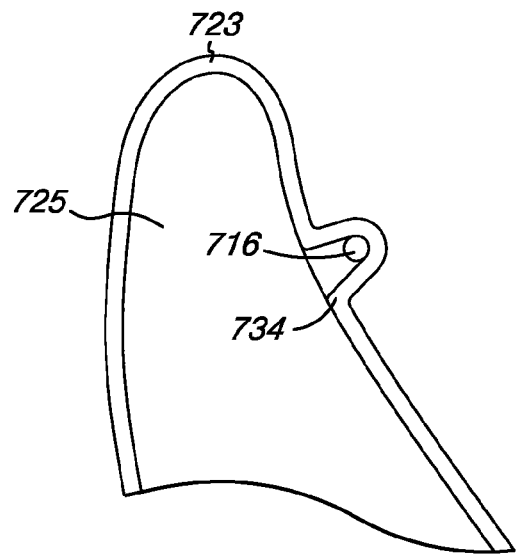
FIG. 7 illustrates a side cut away view taken along line 7-7 of the appliance of FIG. 3B.

FIG. 7 illustrates a side cut away view taken along line 7-7 of the appliance of FIG. 3B. The illustration of FIG. 7 similarly shows that the shell is formed such that the appliance 723 can be lifted over the wire 716 to remove the appliance from the teeth 725 and leaving the wire in place. In some embodiments, the appliance may have a slit cut into the surface of the appliance to allow the wire to pass through the appliance as it is lifted off.

Accordingly, in some embodiments, a wire attachment appliance, can include a shell having one or more cavities formed therein and shaped to receive one or more teeth, at least two wire attachment members provided on the shell, and at least one attachment material reservoir provided on the shell, wherein the attachment material is provided to attach a wire to a tooth adjacent to a particular reservoir of the at least one attachment material reservoirs.

In some such embodiments, the appliance includes a wire having portions of the wire positioned in the wire attachment members and having other portions of the wire positioned within the one or more attachment material reservoirs.

In the illustrated embodiments of FIGS. 3A-8, the cavities formed around the teeth are illustrated to extend around the entire circumference of the tooth and presumed to cover each tooth on each side from top of the tooth to at least the gum line. However, the embodiments of the present disclosure should not be limited to such shapes.

In some embodiments, the cavity may be formed by a ring of material formed to fit around a tooth where the top of the tooth is not covered by shell material. In some embodiments, at least one of the one or more cavities is formed including at least one side surface and wherein the at least one side surface includes a portion that is shaped to abut an exterior surface of one of the one or more teeth. Further, in some embodiments, at least one of the cavities covers a top and portions of each of a number of side surfaces of one of the one or more teeth, as illustrated in the embodiments of FIGS. 3A-8.

In some embodiments, the shell and the wire attachment members and/or the one or more attachment material reservoirs can be provided as a unitary body. This can be accomplished, for example, by forming the shell and wire attachment members together or by forming the shell around the wire attachment members, or embedding the wire attachment members in the shell material.

As discussed herein, the wire can be provided by any suitable material. For example, a wire can be a metallic wire, can be another wire type, such as multiple wire strands woven together, or can be from another material such as a polymer or composite material. As discussed above, in some embodiments, at least one of the attachment material reservoirs can include an aperture for the placement of a material dispenser therein.

In some embodiments, the shell, or portions thereof, can be constructed from a transparent material. This can be beneficial, for example, where a treatment profession may be able to see the positioning of the wire and/or the curing state of a curable attachment material provided to one or more of the reservoirs. This can be particularly beneficial in embodiments where the wire is positioned on the lingual side of the teeth, since it can be difficult to for the treatment professional to see in that area of the mouth of the patient, among other areas of the mouth.

Figure 8:
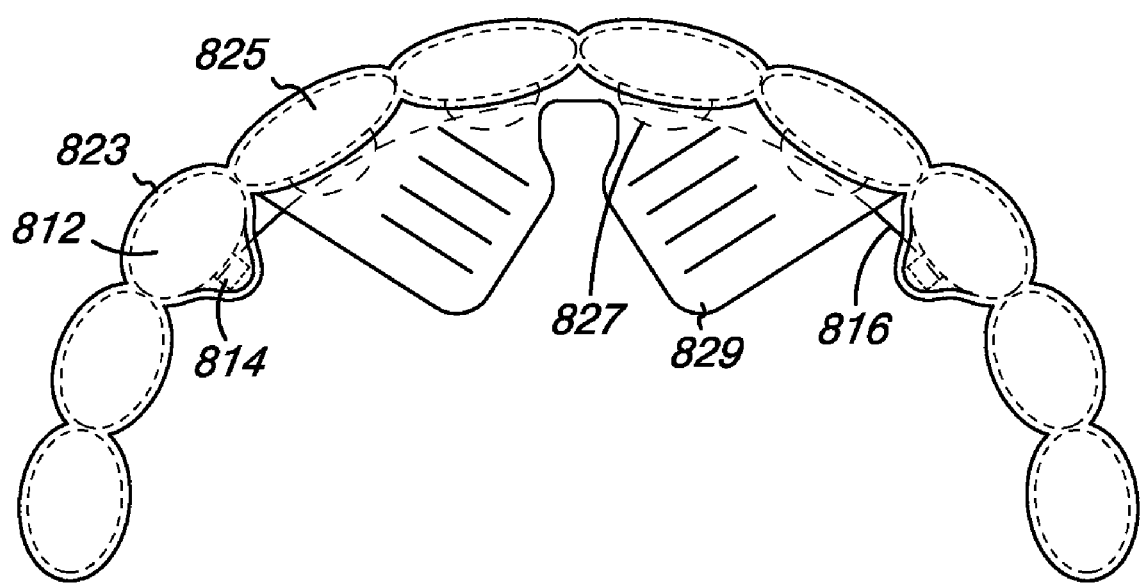
FIG. 8 is a top view illustrating an appliance positioned over a jaw of a patient and having a number of tabs formed thereon according to an embodiment of the present disclosure.

FIG. 8 is a top view illustrating an appliance positioned over a jaw of a patient and having a number of tabs 829 formed thereon according to an embodiment of the present disclosure. In such embodiments, the tabs 829 can be beneficial, for example, to help a treatment professional lift the appliance 823 over the wire attachment members 814, the wire 816, and the attachment members 827 once formed and off teeth 812 and 825. In such embodiments, a portion or all of the appliance can be fabricated from transparent materials to aid the treatment professional in viewing some areas of the mouth.

Figure 9:
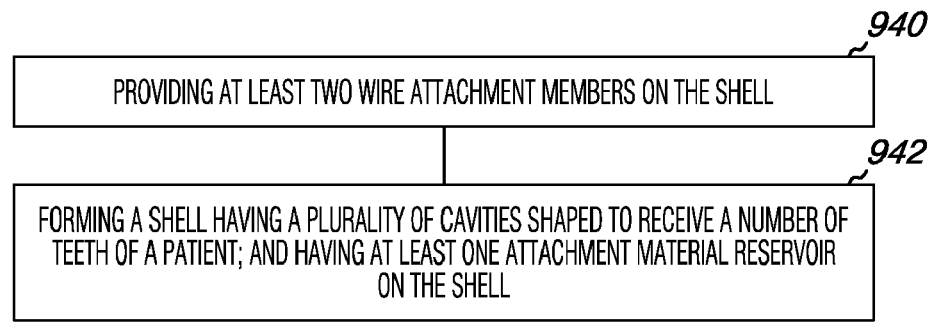
FIG. 9 illustrates a method embodiment of forming a wire attachment appliance according to the present disclosure.

FIG. 9 illustrates a method embodiment of forming a wire attachment appliance according to the present disclosure. In the embodiment of FIG. 9, the method includes providing at least two wire attachment members on the shell, at block 940. At block 942, the method includes forming a shell having a plurality of cavities shaped to receive a number of teeth of a patient and having at least one attachment material reservoir on the shell.

In some embodiments, each particular attachment material reservoir can be positioned such that when an attachment material is provided the reservoir, the attachment material can contact a surface of a tooth adjacent to the particular reservoir. This arrangement can be used to attach a wire to the tooth adjacent to the particular reservoir.

In some embodiments, a method can include forming a virtual model of one or more of the number of teeth, as described above. In various embodiments, a method can include creating a physical model based upon the virtual model.

In such embodiments, the method can include attaching the wire attachment members to the physical model. A method can include applying shell formation material over at least a portion of the physical model and the wire attachment members to form the shell having the wire attachment members provided on the shell.

Figure 10:
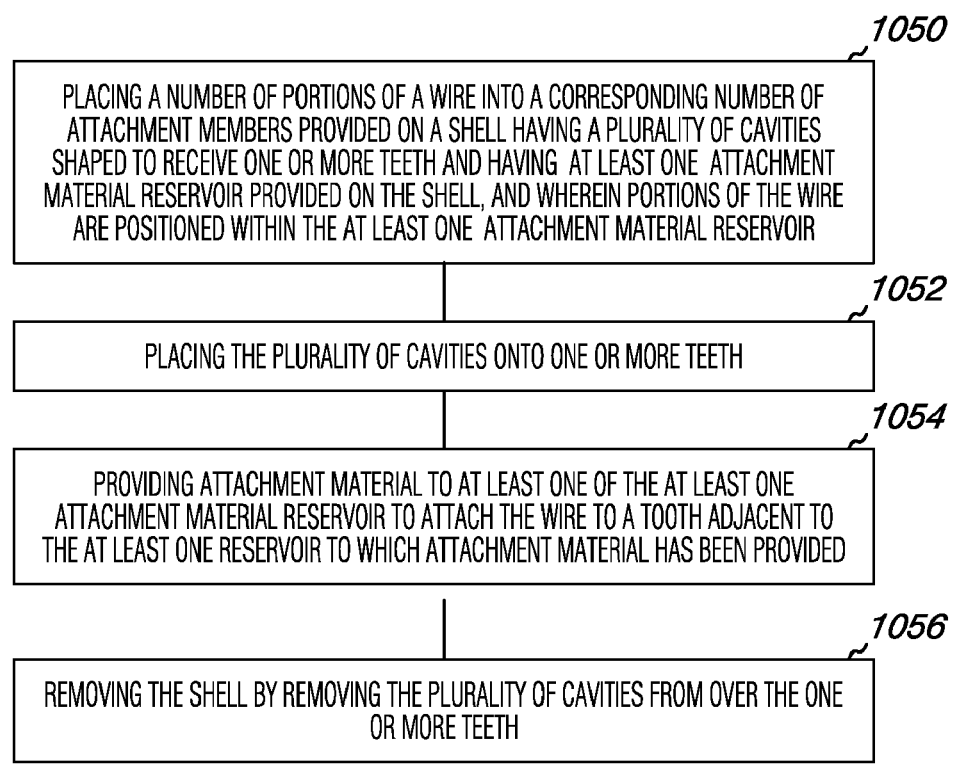
FIG. 10 illustrates another method embodiment of attaching a wire according to the present disclosure.

FIG. 10 illustrates another method embodiment of attaching a wire according to the present disclosure. In the embodiment of FIG. 10, the method includes placing a number of portions of a wire into a corresponding number of wire attachment members provided on a shell having a plurality of cavities shaped to receive one or more teeth and having at least one attachment material reservoirs provided on the shell, and wherein portions of the wire are positioned within the at least one attachment material reservoirs, at block 1050. At block 1052, the method includes, placing the plurality of cavities onto one or more teeth.

The method embodiment of FIG. 10 also includes, providing attachment material to at least one of the at least one attachment material reservoirs to attach the wire to a tooth adjacent to the at least one reservoirs to which attachment material has been provided, at block 1054. At block 1056, the method includes removing the shell by removing the plurality of cavities from over the one or more teeth.

In such embodiments, removing the shell can, for example, include removing the shell and the number of wire attachment members provided on the shell by removing the plurality of cavities from over the one or more teeth. Removing the shell can include lifting one or more tabs to remove the plurality of cavities from over the one or more teeth.

In some embodiments, providing attachment material can include providing a curable composite material to at least one of the number of attachment material reservoirs. Providing curable composite material can, for example, include providing a light curable composite material.

The curable composite material can be a flowable curable composite material. This can be beneficial in, for example, filling the reservoirs to create the attachment member. Moldable materials may also be useful in some embodiment. Some suitable materials can be both flowable and moldable and such characteristics typically depend upon the viscosity of the material.

In some embodiments, a curable composite material can be used to attach the wire to the tooth adjacent to the at least one reservoirs to which attachment material has been provided.

As will further be appreciated by one of ordinary skill in the relevant art, various features are grouped together in the description of the present disclosure in a single embodiment for the purpose of streamlining the disclosure. This method of disclosure, however, is not to be interpreted as reflecting an intention that the embodiments of the disclosure require more features than are expressly recited in each of the following claims. Rather, as the claim recitations reflect, inventive subject matter lies in less than all features of a single disclosed embodiment.

Hence, predetermining a treatment plan with a virtual model as described in the present disclosure may be a recommended and claimed methodology, however, just forming and/or using an appliance as described in the disclosure and as recited in the following claims is intended as novel subject matter to be protected. For example, novel subject matter as described in the present disclosure can be included in a portion of an appliance, rather than the whole appliance, and remain consistent with the teachings of the present disclosure.

Unless explicitly stated, the method embodiments described herein are not constrained to a particular order or sequence. Additionally, some of the described method embodiments, or elements thereof, can occur or be performed at the same, or at least substantially the same, point in time.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A wire attachment appliance, comprising:
   a shell formed of a particular material having a plurality of cavities formed therein and shaped to receive one or more teeth;
   at least two wire attachment members located within at least two of the plurality of cavities;
   at least one attachment material reservoir formed with the shell and located on an interior surface of at least one other of the plurality of cavities, wherein attachment material, different than the particular material, is provided to attach a wire to a tooth adjacent to the at least one attachment material reservoir; and
   the wire, having portions positioned in the at least two wire attachment members and having other portions positioned within the at least one attachment material reservoir.

2. The appliance of claim 1, wherein at least one of the plurality of cavities is formed including at least one side surface and wherein the at least one side surface includes a portion that is shaped to abut an exterior surface of one of the one or more teeth.

3. The appliance of claim 1, wherein the wire is a metallic wire.

4. The appliance of claim 1, wherein at least one of the at least one attachment material reservoir includes an aperture for the placement of a material dispenser therein.

5. The appliance of claim 4, wherein the aperture is sized for the placement of a material dispenser needle tip therein.

6. The appliance of claim 1, wherein at least one of the at least one attachment material reservoir includes an aperture for the venting of air therethrough.

7. The appliance of claim 1, wherein the particular material is a transparent material.

8. The appliance of claim 1, wherein at least one of the plurality of cavities covers a top and portions of each of a number of side surfaces of one of the one or more teeth.

9. The appliance of claim 1, wherein the shell and the at least two wire attachment members are provided as a unitary body.

10. The appliance of claim 1, wherein the shell and the at least one attachment material reservoirs are provided as a unitary body.

11. The appliance of claim 1, wherein the shell, the at least two wire attachment members, and the at least one attachment material reservoir are provided as a unitary body.

12. The appliance of claim 1, wherein the shell includes a number of tabs to aid in lifting the appliance off of the number of teeth.

13. A method of forming a wire attachment appliance, the method comprising:
   forming a shell having a plurality of cavities shaped to receive a number of teeth of a patient, the shell having at least one attachment material reservoir within at least one of the plurality of cavities, wherein the at least one attachment material reservoir is positioned such that when an attachment material is provided thereto, the attachment material contacts a surface of a tooth adjacent to the particular reservoir to attach a wire to the tooth adjacent to the particular reservoir; and
   including at least two wire attachment members on an interior surface of at least two other of the plurality of cavities.

14. The method of claim 13, wherein the method includes forming a virtual model of one or more of the number of teeth.

15. The method of claim 14, wherein the method includes creating a physical model based upon the virtual model.

16. The method of claim 15, wherein the method includes attaching the at least two wire attachment members to the physical model.

17. The method of claim 16, wherein the method includes applying shell formation material over at least a portion of the physical model and the at least two wire attachment members to form the shell having the at least two wire attachment members included on the shell.

18. The method of claim 13, wherein including the at least two wire attachment members includes positioning the at least two wire attachment members on the interior surface of the at least two of the plurality of cavities after the shell is formed.

19. The method of claim 17, wherein the method includes attaching the wire to the at least two wire attachment members before the shell formation material is applied over at least the portion of the physical model.

20. A method of attaching a wire, the method comprising:
   placing a number of portions of a wire into a corresponding number of wire attachment members located within a shell having a plurality of cavities shaped to receive one or more teeth and having at least one attachment material reservoir formed with the shell, and wherein portions of the wire are positioned within the attachment material reservoir;
   placing the plurality of cavities onto one or more teeth;
   providing attachment material to at least one of the at least one attachment material reservoir while the plurality of cavities are placed onto the one or more teeth to attach the wire to a tooth adjacent to the at least one reservoir to which attachment material has been provided; and
   removing the shell by removing the plurality of cavities from over the one or more teeth.

21. The method of claim 20, wherein removing the shell includes removing the shell and the number of wire attachment members provided on the shell by removing the plurality of cavities from over the one or more teeth.

22. The method of claim 20, wherein removing the shell includes lifting one or more tabs to remove the plurality of cavities from over the one or more teeth.

23. The method of claim 20, wherein providing attachment material includes providing a curable composite material to at least one of the attachment material reservoirs.

24. The method of claim 23, wherein providing curable composite material includes providing a light curable composite material.

25. The method of claim 23, wherein providing curable composite material includes providing a flowable curable composite material.

26. The method of claim 23, wherein the method includes curing the curable composite material to attach the wire to the tooth adjacent to the at least one reservoirs to which attachment material has been provided.

\* \* \* \* \*